United States Patent [19]

Keith et al.

[11] 4,321,252

[45] Mar. 23, 1982

[54] POLYMERIC DIFFUSION MATRIX CONTAINING ESTER DERIVATIVES OF ESTRADIOL

[75] Inventors: Alec D. Keith, Miami, Fla.; Wallace Snipes, State College, Pa.

[73] Assignee: Key Pharmaceuticals, Inc., Miami, Fla.

[21] Appl. No.: 217,400

[22] Filed: Dec. 17, 1980

Related U.S. Application Data

[63] Continuation-in-part of Ser. No. 167,729, Jul. 11, 1980, which is a continuation-in-part of Ser. No. 109,242, Jan. 3, 1980, which is a continuation-in-part of Ser. No. 2,565, Jan. 11, 1979, abandoned.

[30] Foreign Application Priority Data

Aug. 14, 1979 [JP] Japan .................................. 54-103459

[51] Int. Cl.³ ........................ A61F 13/00; A61K 9/70; A61L 15/03; A61K 31/79
[52] U.S. Cl. .................................... 424/28; 128/268; 128/260; 424/78; 424/80
[58] Field of Search .............................. 424/28, 78, 80; 128/268, 260

[56] References Cited

U.S. PATENT DOCUMENTS

| | | | |
|---|---|---|---|
| 2,693,438 | 11/1954 | Ward | 424/28 |
| 3,214,338 | 10/1965 | Ehrlich | 424/28 |
| 3,249,109 | 5/1968 | Maeth | 128/268 |
| 3,287,222 | 11/1966 | Larde et al. | 424/28 |
| 3,598,123 | 8/1971 | Zaffaroni | 128/268 |
| 3,608,070 | 9/1971 | Nouvel | 424/80 |
| 3,627,871 | 12/1971 | Groves et al. | 424/78 |
| 3,731,683 | 5/1973 | Zaffaroni | 128/156 |
| 3,803,300 | 4/1974 | Pospischic | 424/28 |
| 3,892,905 | 7/1975 | Albert | 252/90 |
| 4,210,633 | 7/1980 | Takruri et al. | 424/80 |

FOREIGN PATENT DOCUMENTS

| | | | |
|---|---|---|---|
| 764422 | 8/1971 | Belgium | 424/28 |
| 2239355 | 2/1974 | Fed. Rep. of Germany | |
| 53/7493 | 3/1978 | Japan | 424/28 |
| 53/130421 | 11/1978 | Japan | |
| 1108837 | 4/1968 | United Kingdom | |
| 219116 | 3/1973 | U.S.S.R. | |

OTHER PUBLICATIONS

Victor, et al., Contraception 1977 16(2): 125–135 Collagen Bands: A New Vaginal Delivery System for Contraceptive Steroids.
WO 80/00916 (15.05.80), Teijen Limited Sustained-Release Preparations Used in Adhesive Contact with Wet Surface, 23 pp.

*Primary Examiner*—Shep K. Rose
*Attorney, Agent, or Firm*—Wegner & Bretschneider

[57] ABSTRACT

There is disclosed a polymeric diffusion matrix for the sustained release of an estradiol ester by delivery to a patient requiring uterine wall maintenance or other types of estrogen therapy wherein the matrix comprises a polar plasticizer, polyvinylalcohol, polyvinylpyrrolidone, and a pharmaceutically effective amount of estradiol ester.

17 Claims, No Drawings

POLYMERIC DIFFUSION MATRIX CONTAINING ESTER DERIVATIVES OF ESTRADIOL

CROSS-REFERENCE TO RELATED APPLICATIONS

This application is a continuation-in-part of U.S. application Ser. No. 167,729, filed July 11, 1980, which in turn is a continuation-in-part of U.S. application Ser. No. 109,242, filed Jan. 3, 1980, which in turn is a continuation-in-part of U.S. application Ser. No. 2,565, filed Jan. 11, 1979, now abandoned.

SUMMARY OF THE INVENTION

The present invention relates to a polymeric diffusion matrix containing estradiol esters. More particularly, the invention relates to a polymeric diffusion matrix containing an estradiol ester characterized by a sustained release of the estradiol esters.

A self-supporting polymeric diffusion matrix is provided for the sustained release of estradiol ester in order to deliver said estradiol ester to a patient and provide said patient with a uterine wall maintenance effect, said matrix comprising from about 2 to about 60% by weight of a polar plasticizer; from about 6 to about 20% by weight polyvinylalcohol; from about 2 to about 10% by weight polyvinylpyrrolidone; and a pharmaceutically effective amount of estradiol ester to provide a sustained release of said estradiol ester over a prolonged period.

In one embodiment the polar plasticizer is glycerol present in an amount of from about 2 to about 60% by weight. In another embodiment the polar plasticizer is polyethylene glycol present in an amount of from about 2 to about 15% by weight. A still further embodiment contemplates a mixture of glycerol and polyethylene glycol wherein the latter is present in an amount by weight of from about 1 to about 5 parts per weight glycerol.

The self-supporting polymeric diffusion matrix generally contains a mixture of polyvinylalcohol and polyvinylpyrrolidone, although it will be understood that other polymeric mixtures may be used provided they yield the desired sustained release effect. For example, both the polyvinylalcohol and the polyvinylpyrrolidone may be completely replaced with from about 1 to about 9% agar or agarose, and preferably from about 1.5 to 3% agar or agarose, 2% agar or agarose being particularly preferred.

As the polyvinylalcohol used in the present invention, there is generally contemplated one having a molecular weight from about 50,000 to about 150,000, and more preferably about 100,000 to about 150,000, 115,000 having been used in related systems of the present inventors with success. The polyvinylalcohol should be hydrolyzed, generally at least to the extent of 90% with a preferred embodiment being at least 95% hydrolyzed. Polyvinylpyrrolidone should have a molecular weight of from about 15,000 to about 85,000, and more preferably from about 20,000 to about 60,000. Polyvinylpyrrolidone with a molecular weight of 40,000 is a particularly preferred embodiment.

The amount by weight of the ingredients other than the polar plasticizer generally should be in the following ranges: Polyvinylalcohol is generally present in an amount of from about 6 to about 20% by weight, with 10% being a preferred embodiment; polyvinylpyrrolidone is present generally in an amount of from about 2 to about 10% by weight.

The water-soluble polymer can be replaced with (in addition to agar) gum arabic, gum tragacanth, polyacrylic acid, polymethacrylic acid, polyvinyloxazolidone, polyvinylmorpholinone, and polyvinylpiperiodone.

Polyalkylene glycols such as polyethylene glycol and polypropylene glycol may replace all or part of the glycerol.

It is possible to replace the polyvinylalcohol with polymers of hydroxyethylacrylate, polymers of hydroxyethylmethacrylate, polymers of hydroxypropylacrylate, and polymers of hydroxypropylmethacrylate.

The estradiol ester derivatives suitable for use according to this invention are pharmacologically acceptable esters, particularly the 3-benzoate and 3-valerate esters of estradiol. Estradiol diacetate may also be used. The esters suitable for this invention provide a source of pharmacologically active estradiol in the bloodstream. It must also be understood that the estradiol esters contemplated herein may be administered in admixture with other drugs which are not incompatible with the desired therapeutic objective.

In forming the matrix, excess water is not required. In accordance with a preferred aspect of the present invention, about 2% by weight estradiol source is included in the diffusion matrix. The resultant homogenous mixture is poured into forms preferably made of glass of stainless steel. For transdermal application a diffusion matrix with a thickness of about 1 to about 3 mm is in accordance with a preferred aspect of this invention. This diffusion matrix can be cut to obtain the desired surface area once it is suitably cured. In accordance with another preferred aspect of this invention the homogenous mixture is poured into oval shaped forms 1 cm thick, the overall dimensions of which are suitable for insertion into the vaginal canal for delivery of the drug in the vicinity of the cervix.

The following methods may be used for preparing the diffusion matrix of the present invention.

In a first method, the matrix is formed at atmospheric pressure. Water and glycerol are first mixed together.

A polar plasticizer such as glycerol is a necessary component in the matrix. A matrix formed without a polar plasticizer is not flexible and has poor diffusional contact with the skin, causing unreliable diffusion release.

The polyvinylalcohol and polyvinylpyrrolidone are then added to the polar plasticizer-water mixture at room temperature with agitation. The mixture is heated to a temperature within the range of from 90° to about 95° C. at atmospheric pressure to extend the polymers. If desired the mixture may be maintained at an elevated temperature for a period of time, based on polymer stability, prior to addition of the drug. Thus, the mixture is stable for a period of time and may be kept for such a period before being mixed with the drug to be delivered to the patient. Thereafter, the mixture is temperature-adjusted and the drug to be applied to the patient is then added to the mixture, with thorough agitation. Once a homogenous mixture of the polymer solution and drug is obtained, the mixture is ready to be cast to form in a drug-containing diffusion matrix. After casting the mixture is cooled to a temperature such that gelation occurs.

It has been found that curing is facilitated by subjecting the matrix to a temperature down to about −20° C.

immediately after casting. The setting period is quickened considerably.

Sodium dodecyl sulfate or sorbitan (Tween-20) or other detergents may be added in an amount of 0.1 to 10% by weight, based on the matrix, as a dispersing agent, if desired.

An absorption facilitator to insure skin penetration such as dimethylsulfoxide, decylmethylsulfoxide, or other penetration enhancers may be added.

The present drug delivery device comprises the drug-containing diffusion matrix which can either be inserted into the vagina in the form of a self supporting vaginal insert or applied as a transdermal patch with means for fastening the matrix to the skin of a patient. Such means can take various forms, such as an occlusive backing layer forming a kind of "bandage" with the diffusion matrix being held against the skin of a patient being treated. A polyethylene or Mylar tape is contemplated as one form of occlusive layer in accordance with the present invention. It can also take the form of an elastic band, such as a cloth band, a rubbery band or other material. Here, the diffusion matrix is placed directly on the skin and held in place over the arm or wrist of the patient. An intermediate adhesive layer between the diffusion matrix and the skin capable of permitting the transdermal application of the drug can also be used.

The invention is illustrated by the following non-limiting examples:

EXAMPLE I

Together there are mixed 20 gm glycerol and 55 ml water. This mixture is heated to 90° C.; after reaching at least 70° C. There are slowly added 15 gm polyvinylalcohol (PVA 100% hydrolyzed, molecular weight 115,000) and 8 gm polyvinylpyrrolidone (mw 40,000). The mixture is stirred at 90° C. until solution is effected, which may take about 10 minutes; it will be appreciated that with larger quantities, a considerably longer period of time may be needed. 98 ml of this solution is then mixed with 2 gm estradiol diacetate, this mixture then being mechanically stirred until homogenious. The homogenous mixture is then poured into forms made of glass or stainless steel which serve as templates to produce a diffusion matrix having a thickness of about 1 to 2 mm. This diffusion matrix is then cut into square pieces of about 1 inch on each side, i.e., to provide a total surface area of about 6.5 cm².

The diffusion matrix is applied to the skin of a patient in need of uterine wall maintenance, the estradiol ester derivative being transdermally delivered. The diffusion matrix is ideally applied to the skin of the patient by means of a single-piece bandage having the diffusion matrix in the center under the occlusive layer, the bandage being provided to the patient with a peel-off cover much like a "band-aid".

EXAMPLE II

Instead of casting the fluid homogenous drug containing matrix with a 1 to 2 mm thickness as disclosed in Example I, it is poured into oval forms 1 cm thick. The cured diffusion matrix is applied in the form of a vaginal insert into a patient in need of uterine wall maintenance, the estradiol ester derivative being delivered in the vicinity of the cervix of the patient.

EXAMPLE III

In place of the glycerol of Example I, there is substituted 10 gm polyethylene glycol having a molecular weight of 1000 and 10 ml water. The resultant diffusion matrix is more rigid than that of Example I, thus improving its ease of application in the form of a vaginal insert.

EXAMPLE IV

In place of the glycerol of Example I, there is substituted 5 gm polyethylene glycol (mw 1000), 4 gm glycerol, and 11 ml water. The resultant diffusion matrix shares the improved rigidity of the diffusion matrix of Example III, while providing contact with the skin characteristic of the glycerol. This type of diffusion matrix is particularly suitable for transdermal application.

EXAMPLE V

In place of the polyvinylalcohol and polyvinylpyrrolidone of Example I, there is substituted 2 gm agarose and 21 ml water, yielding a diffusion matrix for the delivery of estradiol ester derivative.

While the above Examples have used estradiol diacetate as the estradiol ester, it must be understood that estradiol 3-benzoate and estradiol 3-valerate are administered in exactly the same fashion, as would be other pharmacologically active estradiol esters. This invention is not, therefore, limited to the particular estradiol esters disclosed herein, but provides a suitable vehicle for the administration of estradiol esters of any pharmacologically active type small enough to pass through the skin.

What is claimed is:

1. A self-supporting polymeric diffusion matrix for the sustained release of a pharmacologically acceptable estradiol in order to deliver said estradiol ester to a patient and provide said patient with a uterine wall maintenance effect, said matrix comprising from about 2 to about 60% of a polar plasticizer, from about 6 to about 20% by weight polyvinylalcohol, from about 2 to about 10% by weight polyvinylpyrrolidone, and a pharmaceutically effective amount of the estradiol ester to provide a sustained release of said estradiol ester over a prolonged period.

2. The polymeric diffusion matrix of claim 1, wherein the estradiol ester is selected from the group consisting of estradiol 3-benzoate, estradiol 3-valerate and estradiol diacetate.

3. The polymeric diffusion matrix of claim 1 or 2 wherein said polar plasticizer is glycerol.

4. The polymeric diffusion matrix of claim 3 wherein said polyvinylalcohol has a molecular weight of about 50,000 to about 150,000.

5. The polymeric diffusion of claim 3 wherein said polyvinylalcohol has a molecular weight of about 100,000 to about 150,000.

6. The polymeric diffusion matrix of claim 3 wherein said polyvinylpyrrolidone has a molecular weight of from about 15,000 to about 85,000.

7. The polymeric diffusion matrix of claim 3 wherein said polyvinylpyrrolidone has a molecular weight of about 20,000 to about 60,000.

8. The polymeric diffusion matrix of claim 3 wherein said polar plasticizer is polyethylene glycol present in an amount of about 1 to about 15% weight.

9. The polymeric diffusion matrix of claim 3 wherein said polar plasticizer is a mixture of glycerol and polyethylene glycol wherein said polyethylene glycol is present in an amount by weight of from about 1 to 5 parts per weight glycerol.

10. A method for the delivery of an estradiol ester selected from the group consisting of estradiol 3-benzoate, estradiol 3-valerate and estradiol diacetate to a patient to provide said patient with a uterine wall maintenance effect, comprising applying in the vicinity of the cervix of said patient a self-supporting diffusion matrix comprising from about 2 to about 60% by weight of a polar plasticizer, from about 6 to about 20% by weight polyvinyl alcohol, from about 2 to about 10% by weight polyvinylpyrrolidone and a pharmaceutically effective amount of the estradiol ester to provide a sustained release of the estradiol ester over a prolonged period.

11. The method of claim 10 wherein said estradiol ester is present in an amount to provide sustained release of about 0.1 to about 1 mg of the estradiol ester per day.

12. A method for the transdermal delivery of an estradiol ester selected from the group consisting of estradiol 3-benzoate, estradiol 3-valerate and estradiol diacetate to a patient to provide said patient with an increased blood level of estradiol comprising applying to said patient a self-supporting diffusion matrix comprising from about 2 to about 60% by weight of a polar plasticizer, from about 6 to about 20% by weight polyvinyl alcohol, from about 2 to about 10% by weight polyvinylpyrrolidone and a pharmaceutically effective amount of the estradiol ester to provide a sustained release of the estradiol ester over a prolonged period.

13. The method of claim 12 wherein said estradiol ester is present in an amount to provide sustained release of about 0.05 to about 1 mg of the estradiol ester per day.

14. A method for the transdermal delivery of an estradiol ester selected from the group consisting of estradiol 3-benzoate, estradiol 3-valerate and estradiol diacetate to a patient for the treatment or prevention of diseases associated with estradiol deficiency to provide said patient with an increased blood level of estradiol comprising applying to said patient a self-supporting diffusion matrix comprising from about 2 to about 60% by weight of a polar plasticizer, from about 6 to about 20% by weight polyvinylalcohol, from about 2 to about 10% by weight polyvinylpyrrolidone and a pharmaceutically effective amount of the estradiol ester to provide a sustained release of the estradiol ester over a prolonged period.

15. The method of claim 14 where the disease condition to be treated or prevented is osteoporosis.

16. A method for the intravaginal delivery of a estradiol ester selected from the group consisting of estradiol 3-benzoate, estradiol 3-valerate and estradiol diacetate to a patient for the treatment or prevention of diseases associated with estradiol deficiency to provide said patient with an increased blood level of estradiol comprising applying to said patient a self-supporting diffusion matrix comprising from about 2 to about 60% by weight of a polar plasticizer, from about 6 to about 20% by weight polyvinylalcohol, from about 2 to about 10% by weight polyvinylpyrrolidone and a pharmaceutically effective amount of the estradiol ester to provide a sustained release of estradiol over a prolonged period.

17. The method of claim 16 where the disease condition to be treated or prevented is osteoporosis.

* * * * *